(12) United States Patent
Chen

(10) Patent No.: US 6,859,034 B2
(45) Date of Patent: Feb. 22, 2005

(54) TIME-DOMAIN DATA INTEGRATION OF MULTIPLE GRADIENT, MULTIPLE TE ECHO TRAINS

(75) Inventor: Songhua Chen, Katy, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 10/435,419

(22) Filed: May 9, 2003

(65) Prior Publication Data

US 2004/0222791 A1 Nov. 11, 2004

(51) Int. Cl.$^7$ .................................................. G01V 3/00
(52) U.S. Cl. ...................................................... 324/303
(58) Field of Search ................................ 324/303, 306, 324/300, 318, 322

(56) References Cited

U.S. PATENT DOCUMENTS

| | | | |
|---|---|---|---|
| 4,710,713 A | 12/1987 | Strikman | 324/303 |
| 4,717,877 A | 1/1988 | Taicher et al. | 324/303 |
| 5,212,447 A | 5/1993 | Paltiel | 324/300 |
| 5,698,979 A | 12/1997 | Taicher et al. | 324/303 |
| 6,107,796 A | 8/2000 | Prammer | 324/303 |
| 6,316,940 B1 | 11/2001 | Akkurt | 324/303 |
| 6,366,087 B1 * | 4/2002 | Coates et al. | 324/303 |
| 6,377,042 B1 | 4/2002 | Menger et al. | 324/303 |
| 6,512,371 B2 * | 1/2003 | Prammer | 324/303 |
| 6,650,114 B2 * | 11/2003 | Kruspe et al. | 324/303 |
| 2002/0163334 A1 | 11/2002 | Hagiwara | 324/303 |
| 2003/0071617 A1 | 4/2003 | Kruspe et al. | 324/303 |

* cited by examiner

Primary Examiner—Louis Arana
(74) Attorney, Agent, or Firm—Madan, Mossman & Sriram, P.C.

(57) ABSTRACT

When NMR spin echo measurements are obtained with one or more of (i) different echo intervals, (ii) different static field gradients, (iii) different polarization times, or (iv) noise levels, due to fluid diffusivity, the spin echo measurements cannot be simply combined. However, by applying a correction factor, such a combination is possible, giving an improved interpretation of the formation properties.

36 Claims, 8 Drawing Sheets

TIME-DOMAIN DATA INTEGRATION OF MULTIPLE GRADIENT, MULTIPLE TE ECHO TRAINS

BACKGROUND OF THE INVENTION

1. Field of the Invention

The present invention relates to a method of obtaining a parameter from nuclear magnetic resonance measurement data. Specifically, the invention improves log acquisition efficiency and formation evaluation in stacked signals obtained from s multiecho sequences from various regions of magnetic field gradient.

2. Description of the Related Art

A new generation of multi-frequency nuclear magnetic resonance (NMR) logging instruments is capable of acquiring data useful for characterizing both formation rock properties (e.g., porosity, bound and movable fluids, and permeability) and reservoir fluid properties. However, acquiring data for both of these characterization goals often requires a diverse assortment of NMR acquisition parameters and sequences. High-resolution formation characterization requires acquisition schemes that generate high S/N echo data without compromising vertical resolution. Fluid properties usually vary more slowly with depth than rock properties, but obtaining fluid properties requires NMR echo data acquisition that maximizes fluid contrasts (e.g. differences between gas, oil, and water). Said data acquisition is best achieved by optimally varying combinations of the magnetic field gradients (G), the inter-echo spacing (TE), and the polarization time (TW) in the acquisition scheme.

NMR logging is based on the static and dynamic aspects of nuclear spins in the presence of a static magnetic field and under the influence of RF excitations. When an assembly of magnetic moments, such as those of hydrogen nuclei, are exposed to a static magnetic field, they tend to align along the direction of the magnetic field, resulting in a bulk magnetization. The rate at which equilibrium is established in such bulk magnetization upon provision of a static magnetic field is characterized by the parameter known as the spin-lattice relaxation time, $T_1$. Another related and frequently used NMR logging parameter is the spin-spin relaxation time $T_2$ (also known as transverse relaxation time), which is a characteristic decay time due to inhomogeneities in the local magnetic field over the sensing volume of the logging tool. Both relaxation times, along with the magnetization strength, provide information about the formation porosity, the composition and quantity of the formation fluid, and other parameters. Methods of obtaining NMR measurements in a downhole environment are described in prior art. Useful techniques and apparati for carrying out such techniques are described in U.S. Pat. No. 4,717,877, issued to Taicher and U.S. Pat. No. 4,710,713, issued to Strikman.

Another measurement parameter obtained in NMR logging is the diffusion of fluids in the formation. Generally, diffusion refers to the motion of atoms in a gaseous or liquid state due to their thermal energy. Self-diffusion is an important parameter, since it is inversely related to the viscosity of the fluid, which is a parameter of considerable importance in borehole surveys. In a uniform magnetic field, diffusion has little effect on the decay rate of measured NMR echoes. In the presence of a gradient magnetic field, although diffusional motion is the same as in the case of no field gradient, the rate of dephasing of a nucleus is significantly greater, thereby resulting in a faster rate of decay. This decay rate is dependent on $G^2 D$, where G is the magnetic field gradient and D is the value of diffusivity.

One important petrophysical parameter that can be derived from NMR logs is the bound volume irreducible, BVI. A commonly used method for estimating BVI is described in the prior art. The method uses a $T_{2\ cutoff}$ value for computation such that $$BVI = \int_{T_{2min}}^{T_{2cutoff}} P(T_2) dT_2 \qquad (1)$$

where $P(T_2)$ is the apparent $T_2$ distribution with individual $T_2$ component expressed by $$T_2^{-1} = T_{2B}^{-1} + \rho \frac{S}{V} + T_{2Diff}^{-1}. \qquad (2)$$

where $T_{2B}$ is the relaxation of the bulk fluid, $\rho$ is the surface relaxivity, S is the pore surface area, V is the pore volume, and $T_{2\ Diff}$ is additional decay time due to diffusion effects. The diffusion term $$T_{2Diff}^{-1} = \frac{\gamma^2 G^2 TE^2 D_{fluid}}{12} \qquad (3)$$

depends on (a) field gradient G, which associates with the acquisition frequency; (b) inter-echo time TE, an acquisition parameter; (c) diffusivity D, a fluid property, and, (d) the gyromagnetic ratio, a property dependent on the nuclear species. In NMR logging, usually only proton spin is of interest. Of note is the multiplicative factor G*TE, consisting of two parameters alterable by the operator. Obviously, data that is acquired using a different G*TE factor will result in a different apparent $T_2$ distribution, $P(T_2)$. Equation (1) indicates that if a same $T_{2\ cutoff}$ value is used to compute BVI of the same formation, the results $P(T_2)$ may be dependent on gradient and TE. If the value of G*TE is small, then the $T_{2Diff}^{-1}$ term contributes significantly less to $T_2^{-1}$ in Eq. (2) than either the bulk fluid relaxation term $T_{2B}^{-1}$ or the surface relaxation term $\rho(S/V)$. In such a case, the dependency of $T_2^{-1}$ on diffusion may be negligible. However, if the value of G*TE is large, $T_{2Diff}^{-1}$ can become the dominant contributing term to $T_2^{-1}$.

Without considering the tool and acquisition dependencies, the value of $T_{2\ cutoff}$ depends on the rock surface mineralogy. A common practice is to "calibrate" the $T_{2\ cutoff}$ from laboratory-based NMR measurements. These lab measurements are often carried out in a magnetic field setup in which no external gradient is applied and thus for which there is a negligible contribution of $T_{2\ Diff}^{-1}$. This is in disparity with the external gradient found in logging tool measurements. The combined echo train enables the use of a single $T_{2\ cutoff}$ consistent with laboratory core-NMR derive $T_{2\ cutoff}$, rendering a better means for core-log integration.

U.S. Pat. No. 5,212,447, issued to Paltiel describes a method and apparatus for determining the self-diffusion constant of earth formations penetrated by a wellbore. Paltiel '447 discloses a technique for conducting borehole NMR measurements including the steps of providing a magnetic field gradient at a desired location along a borehole, obtaining at least one and preferably two or more sets of NMR data in the presence of the magnetic field gradient, sensing the diffusion effect on the decay of at least the first echo and determining therefrom the diffusion coefficient. Obtaining at least one set of NMR data includes carrying out two sets of NMR data acquisitions such that the sets differ in at least one of the following parameters: the time the molecules are allowed to diffuse, the magnitude of the magnetic field gradient, and the time over which the pulses are applied (if magnetic field gradient pulses are used).

U.S. Pat. No. 5,698,979, issued to Taicher discloses a method of measuring motion properties of nuclei within pore spaced of a porous medium. The method includes applying a static magnetic field to the medium to polarize the nuclei, generating a first magnitude of magnetic field gradient within the pore spaces of the medium, applying a radio frequency magnetic field to excite the nuclei receiving NMR signals from the nuclei, and calculating the motion properties from rates of decay of the amplitude of the NMR signals. Taicher '979 applies a static magnetic field having a first amplitude, a second amplitude and an amplitude gradient, and sequentially excites nuclei and receives resonance signals at frequencies corresponding to regions defined by the first and second magnetic amplitudes. Motion calculation is determined from differences in rates of decay of the amplitudes of the resonance signals from the first and second frequencies.

U.S. Pat. No. 6,316,940, issued to Akkurt, discloses a method of separating signals from different fluids using user-adjusted measurement parameters. Akkurt '940 is based on forcing diffusion as the dominant relaxation mechanism for the brine phase in NMR measurements of a geologic formation. Certain measurement parameters are changed to enhance the role of diffusion relaxation in the brine phase. The enhanced diffusion relaxation in turn establishes an upper limit for the $T_2$ distribution of the brine phase, which limit can be calculated. Once this upper limit is found, any phase having a $T_2$ longer than the upper limit can be identified unambiguously as not being brine. The measurement parameters that are varied are the inter-echo time TE and the magnetic field gradient G of the tool.

U.S. Pat. No. 6,377,042 issued to Menger, discloses a method and system to obtain enhanced-resolution NMR data by merging, in the time domain, different NMR pulse echo trains into a single echo train. The input echo trains can be acquired with different inter-echo spacing, wait time, and signal-to-noise ratio parameters that are optimized to correspond to both fast and slow portions of the $T_2$ spectrum. The merged echo trains are inverted into complete $T_2$ spectra in a single step thereby overcoming ambiguities and other limitations of prior art methods. In a preferred embodiment, the merging process does not require a priori information about $T_1$, and the merged echo trains are optimized in with respect to $T_2$ resolution. The method of Menger '042 discloses inverting and binning input data including partially recovered and fully recovered data. In a second step, the difference between the invented data is calculated for all bins within a certain range, enabling calculation of an "artificial" echo train, which can be added to the original partially recovered data. In a third step, data is merged to obtain a final echo train, which is provided as an input for standard $T_2$ inversion. In order to obtain a more complete knowledge of rock formation, it is necessary to consider as many parameters as possible, including changes concerning the static magnetic field (i.e. field gradient). Menger '042 address changing echo train parameters, but does not address the effect of a change in the field gradient parameter.

To date, multiple G, TE and TW data are not combined in time-domain processing to obtain formation rock properties. The main obstacle is that different G-TE data cannot be simply stacked. A common practice, dictated in part by hardware limitations of older NMR tools, has been to log multiple passes, each with separate evaluation objectives. Even with multifrequency tools that are capable of acquiring comprehensive data in a single pass, data are not used economically. Thus, in order to satisfy the formation rock and fluid property characterization requirement, one is forced to either log slowly or to compromise the vertical resolution.

Clearly there is a need to develop a method that improves log acquisition efficiency and maximizes economic usage of all data. The present invention addresses the above-mentioned problem.

SUMMARY OF THE INVENTION

The present invention is an apparatus and method of determining a parameter of interest of an earth formation using a logging tool conveyed in a borehole in the formation. Multiecho sequences are acquired from a first and second region of interest using a first and second radio frequency (RF) pulse sequence. A correction factor depending at least in part on a diffusivity of a fluid in the earth formation is determined, and the first and second multiecho sequences are combined using the correction factor to obtain a combined multiecho sequence. The second pulse sequence has at least one parameter different from a parameter of said first pulse sequence and/or a gradient of a static magnetic field in said first region is different from a gradient of a static magnetic field in said second region. In a preferred embodiment of the invention, a multifrequency logging tool is used, the first and second regions are different, and a static magnetic field in said first region is different from a static magnetic field in said second region. The logging tool contains an arrangement for shifting a static magnetic field in the earth formation. Such an arrangement is thereby capable of creating a series of sensitive volumes by acquiring data at different RF frequencies.

The method may be used when the first RF pulse sequence differs from the second RF pulse sequence in at least one of: (i) RF frequency which corresponds to a gradient or gradient distribution, (ii) an interval between refocusing pulses. The method may be used when the polarization time, and/or the number of pulses of the two sequences are the same or different. The correction factor is a multiplicative factor relating the first and second multiecho sequences.

The correction factor is further dependent on at least one of (i) a gradient of a static magnetic field associated with said first RF pulse sequence, (ii) a gradient of a static magnetic field associated with said second RF pulse sequence, (iii) an interecho time associated with said first RF pulse sequence, (iv) an interecho time associated with said second RF pulse sequence, (v) a noise level for said first multiecho sequence, and, (vi) a noise level for said second multiecho sequence.

The fluid diffusivity may be obtained from a measured diffusivity and applying a correction for at least one of (i) a temperature of the fluid, and, (ii) a depth (or pressure) of the fluid.

In optional embodiments of the invention, a time-dependent weighting may be used when there is a difference in a noise level of the first multiecho sequence and the second multiecho sequence.

When the first and second RF pulse sequences differ only in a wait time, it is possible to determine from the combined echo sequence a clay bound water and a capillary bound water volume. When the first and second pulse sequences differ only in frequency, it is possible to determine from the combined echo sequence an entire porosity distribution.

When the first and second regions of interest differ in a gradient of an associated static magnetic field, it is possible to determine from the combined sequence clay-bound water, capillary bound water, and movable fluid volumes.

In a preferred embodiment of the invention, the longest echo train is acquired using the highest frequency. In an optional embodiment of the invention, when a product of a gradient and an interecho time for the first region of interest is different from a product of a gradient and an interecho time for the second region of interest, the method includes applying an interpolation to bring data points to the same density, and applying a time-dependent weighting function.

BRIEF DESCRIPTION OF THE DRAWINGS

The present invention is best understood with reference lo the following figures in which like numerals refer to like elements.

DESCRIPTION OF PREFERRED EMBODIMENT

The method of the present invention integrates different G-TE multiecho sequences in the time domain. The combined multiecho sequences can be used to obtain clay bound water, capillary bound water volume, and total porosity information with improved vertical resolution. The same data, in the uncombined form, are used for fluid property estimation. Thus, the data are used more economically.

Figure 1:
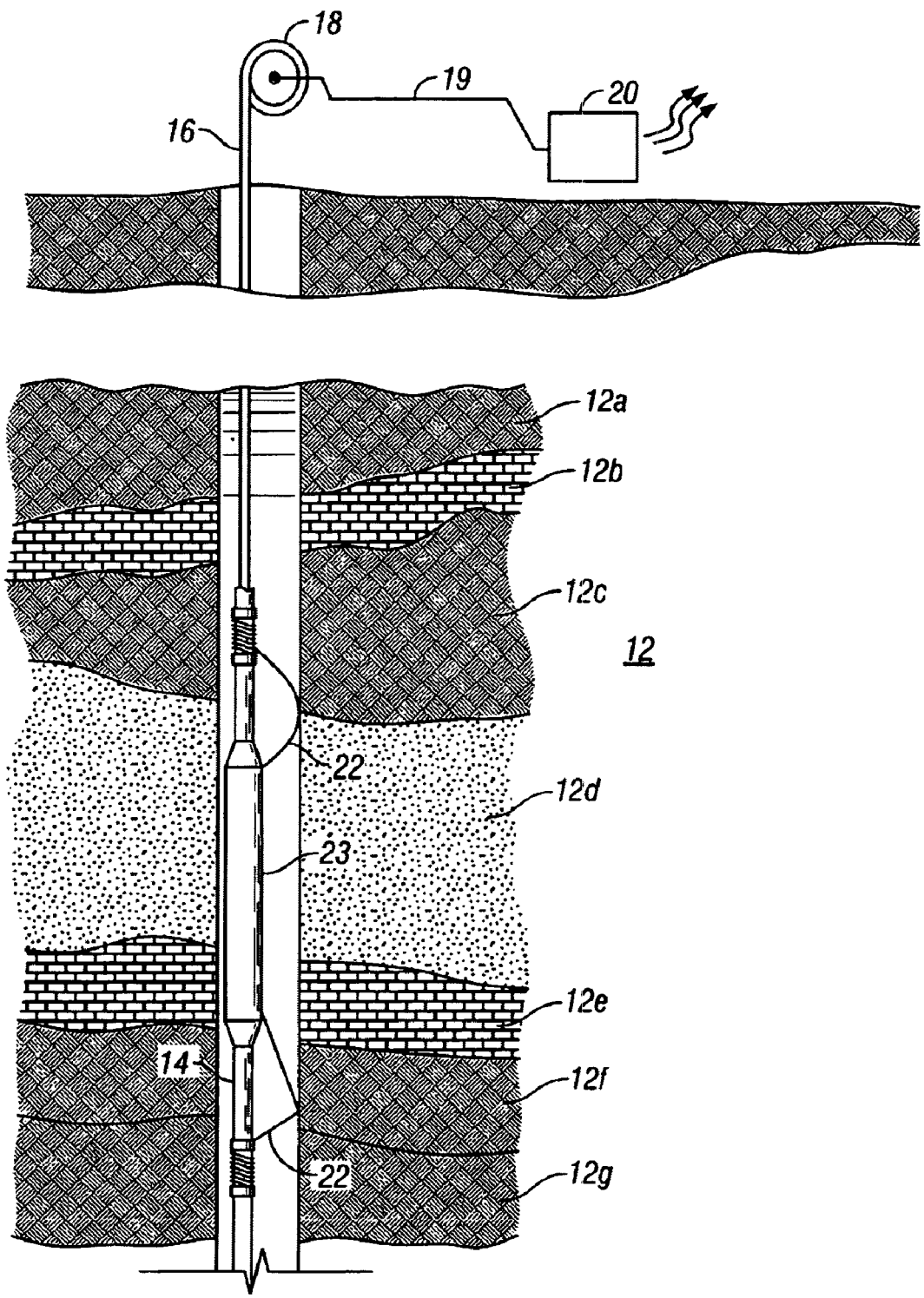
FIG. 1 depicts diagrammatically an eccentric NMR logging tool in a borehole.

FIG. 1 depicts an apparatus that is suitable for use with the present invention. A borehole 10 has been drilled in a typical fashion into a subsurface geological formation 12 to be investigated for potential hydrocarbon producing reservoirs. An NMR logging tool 14 has been lowered into the hole 10 by means of a cable 16 and appropriate surface equipment represented diagrammatically by a reel 18 and is being raised through the formation 12 comprising a plurality of layers 12a through 12g of differing composition, to log one or more of the formation's characteristics. The NMR logging tool is provided with bowsprings 22 to maintain the tool in an eccentric position within the borehole with one side of the tool in proximity to the borehole wall. The permanent magnets used for providing the static magnetic field is indicated by 23 and the magnet configuration is that of a line dipole. Signals generated by the tool 14 are passed to the surface through the cable 16 and from the cable 16 through another line 19 to appropriate surface equipment 20 for processing, recording and/or display or for transmission to another site for processing, recording and/or display.

Figure 2:
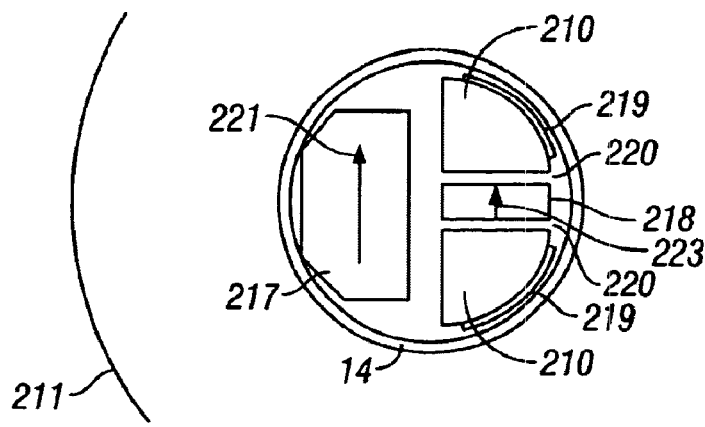
FIGS. 2, 2A, and 2B show configurations of magnets, antenna and shield of the present invention for achieving the desired field configuration.

FIG. 2 schematically illustrates a magnetic configuration that is suitable for use with the present invention to operate over a gradient field. The tool is described in U.S. Pat. No. 6,348,792 to Beard et al, having the same assignee as the present application and the contents of which are fully incorporated herein by reference. It should be pointed out that the method of the present invention is independent of the specific magnet configuration and can be used with either a side-looking or a centralized tool, or even a pad device, as long as the tool operates at a gradient field. The method of the present invention can even be used with a single frequency logging tool. The tool cross-sectional view in FIG. 2 illustrates a main magnet 217, a second magnet 218, and a transceiver antenna, comprising wires 219 and core material 210. The arrows 221 and 223 depict the polarization (e.g., from the South pole to the North pole) of the main magnet 217 and the secondary magnet 218, respectively. A noteworthy feature of the arrangement shown in FIG. 2 is that the polarization of the magnets providing the static field is towards the side of the tool, rather than towards the front of the tool (the right side of FIG. 2) as in prior art devices. The importance of this rotated configuration is discussed below.

The second magnet 218 is positioned to augment the shape of the static magnetic field by adding a second magnetic dipole in close proximity to the RF dipole defined by the wires 219 and the soft magnetic core 210. This moves the center of the effective static dipole closer to the RF dipole, thereby increasing the azimuthal extent of the region of examination, the desirability of which has been discussed above. The second magnet 218 also reduces the shunting effect of the high permeability magnetic core 210 on the main magnet 217. In the absence of the second magnet, the DC field would be effectively shorted by the core 210. Thus, the second magnet, besides acting as a shaping magnet for shaping the static field to the front of the tool, also acts as a bucking magnet with respect to the static field in the core 210. Those versed in the art would recognize that the bucking function and a limited shaping could be accomplished simply by having a gap in the core. However, since some kind of field shaping is required on the front side of the tool, in a preferred embodiment of the invention, the second magnet serves both for field shaping and for bucking. If the static field in the core 210 is close to zero, then the magnetostrictive ringing from the core is substantially eliminated.

Figure 2A:
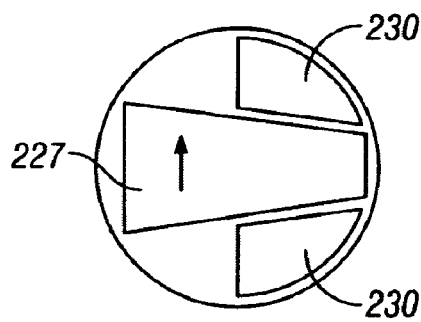
Figure 2B:
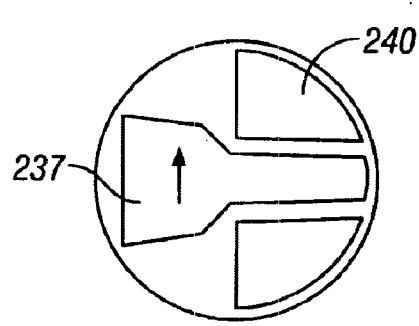

As noted above, within the region of investigation, the static field gradient is substantially uniform and the static field strength lies within predetermined limits to give a substantially uniform Larmor frequency. Those versed in the art would recognize that the combination of field shaping and bucking could be accomplished by other magnet configurations than those shown in FIG. 2. For example, FIG. 2A shows a single magnet 227 and magnetic core 230 that produces substantially the same static field as that produced by the combination of magnets 217 and 218 in FIG. 2. A substantially similar field configuration results from the arrangement in FIG. 2B with the magnet 237 and the core 240. What is being accomplished by the magnet arrangements in FIGS. 2, 2A and 2B is an asymmetry in the static magnetic field in a direction orthogonal to the direction of magnetization. In an optional embodiment of the invention (not shown) the second magnet is omitted.

Returning to FIG. 2, the transceiver wires 219 and core pieces 210 should preferably be separated as far as possible towards the sides of the tool. This separation increases the transceiver antenna efficiency by increasing the effective RF dipole of the antenna and augments the shape of the RF magnetic field isolines so that they better conform to the static magnetic field isolines. The secondary magnet is preferably made of nonconducting material to minimize eddy currents induced by the RF field, thereby increasing the RF antenna efficiency.

The core is preferably made of a powdered soft magnetic material, other than ferrite. It preferably has a high saturation flux density and comprises particles of powdered material small enough to be transparent to the RF magnetic field. Such a material has been described in U.S. Pat. No. 6,452,388, issued to Reiderman et al., the contents of which are fully incorporated herein by reference.

Figure 3:
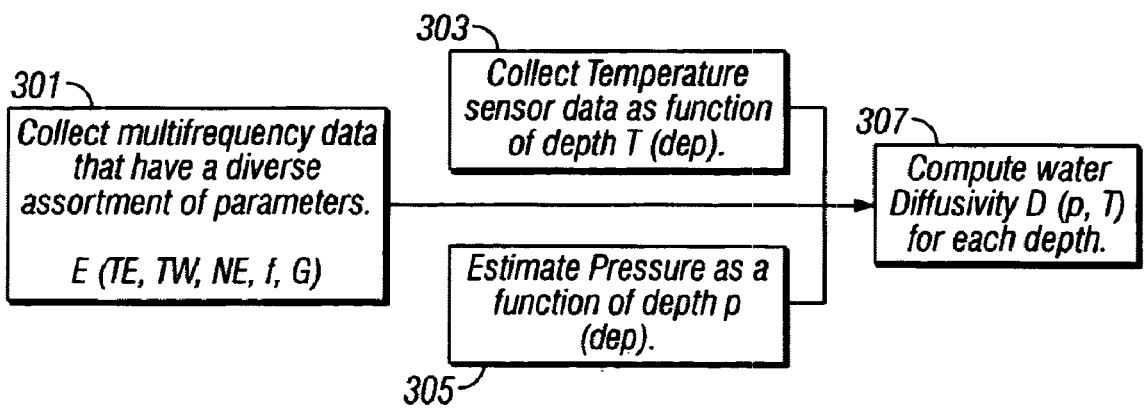
FIG. 3 shows a flowchart of the method of data collection in a preferred embodiment of the invention.

FIG. 3 shows a flowchart of the method of data collection in a preferred embodiment of the invention. In this preferred embodiment, multi-frequency NMR data is collected (301). In an alternative embodiment, multiple echo sequences may be collected at a single frequency with different logging parameters, such as TE. A typical RF pulse sequence can be a CPMG sequence, although in a preferred embodiment of the invention, an optimized refocusing pulse sequence with refocusing pulses having a tipping angle less than 180° is used. Such modified refocusing pulses are described in U.S. Pat. No. 6,163,153 to Reiderman et al, and in U.S. Pat. No. 6,466,013 to Slade et al., both patents having the same assignee as the present invention and the contents of which are incorporated herein by reference. Received signal echoes are affected by an assortment of parameters of the RF field, such as inter-echo time (TE), wait time (TW), number of echoes (NE), RF frequency (f), and static magnetic field gradient (G). The strength of the received signal varies directly with the RF frequency, and each frequency corresponds to a sensitive volume having different magnetic field gradient strength. Due to diffusion, the echo decay of the signal increases as the magnetic gradient increases. The data sampling rate is inversely proportional to TE. The effect that TW has on the signal varies with the degree of polarization, which depends on the type of fluid involved.

Figure 4:
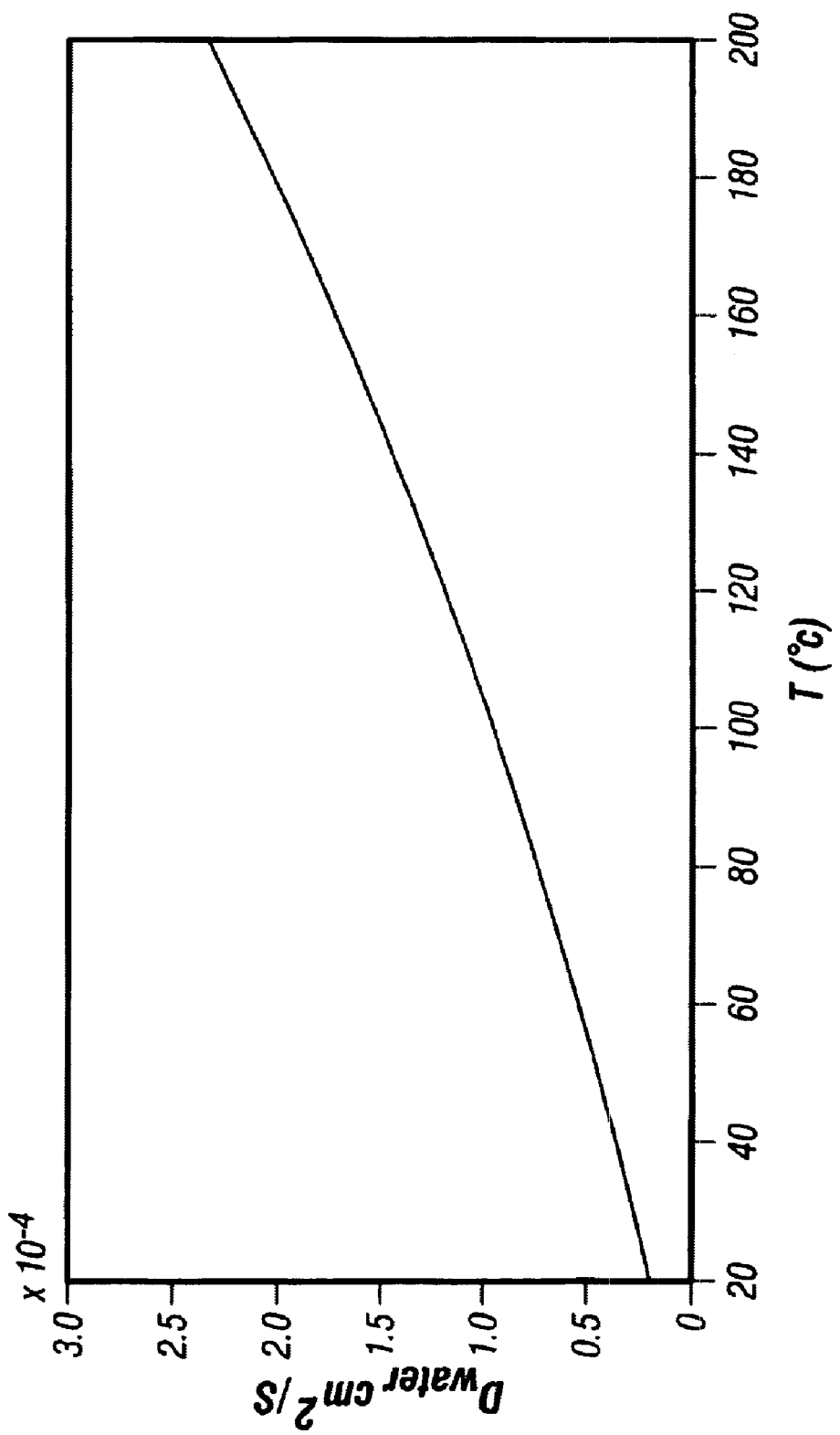
FIG. 4 shows the temperature dependence of water diffusivity.

The temperature and pressure of the well bore, which approximate that of the formation, are required in order to compute the diffusivity of water (brine). Hence, the method of the invention collects temperature as a function of depth (303) and pressure as a function of depth (305). Temperature and pressure contribute to a calculation of water diffusivity (307). Typically, water diffusivity is sensitive to temperature variation but is less sensitive to pressure variation. Therefore, if the pressure data is not collected directly, computation from a hydraulic pressure gradient formula is sufficient for the present application. Furthermore, formation temperatures computed from a geothermal gradient are acceptable in case direct temperature measurement data are not available. The correction factor utilizes the water (brine) diffusivity even though the fluids saturating the formation could contain fluids other than water. The correction method described in the present invention is suitable for capillary bound water volume and CBW estimation, and the fluid in these volume fractions is primarily water. Furthermore, bulk volume movable (BVM) fluid can be computed from the difference between effective porosity (MPHE) and BVI. The uncertainty of fluid types in the formation, which affects the diffusivity, will have a less adverse effect on these key petrophysical parameters. FIG. 4 shows the temperature dependence of water diffusivity, based on published viscosity data and Vinegar's D vs. η correlation. Such viscosity data can be found, for example, in *CRC Handbook of Chemistry and Physics*. A fifth-order polynomial is used for smoothing. Temperature (in ° C.) lies along the abscissa, and Diffusivity of water (in cm$^2$/sec) lies along the ordinate.

Figure 5A:
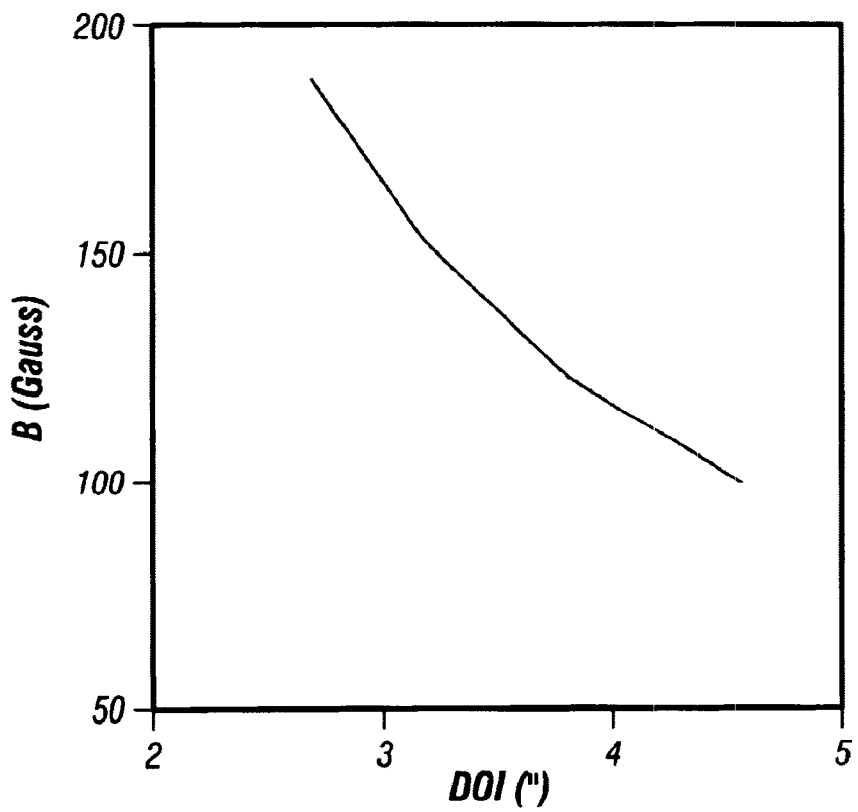
FIGS. 5a and 5b show the magnetic field and gradient strength, respectively, as functions of depth of investigation.
Figure 5B:
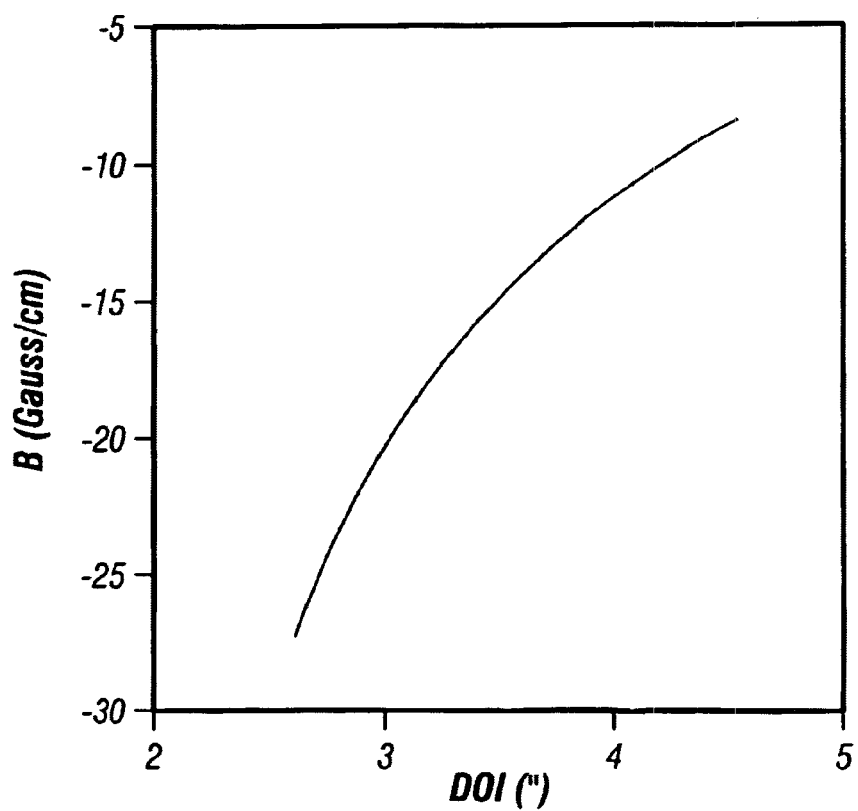

FIG. 5a illustrates the magnetic field strength (B) as a function of depth of investigation (DOI). The magnetic field, along the ordinate axis, is represented in Gauss and the DOI is represented in inches. As the DOI increases the strength of the magnetic field diminishes. FIG. 5b shows the magnetic field gradient (G) over the same DOI, with field gradient (in Gauss/cm) along the ordinate axis and DOI (in inches) along the abscissa. For each acquisition, a set of NMR RF frequencies are selected. For a given hardware configuration, a tool gradient strength is known as a function at each frequency.

Generally, the magnetic field gradient increases with an increase in frequency for a logging tool that has a magnetic field strength distribution that is depicted in FIG. 5. In general, fluids in pore spaces in formation rocks experience a total gradient:

$$\vec{G}_{total} = \vec{G}_{ext} + \vec{G}_{int} \quad (4)$$

that is the vector sum of the external and internal gradients. The internal gradient arises due to differences in magnetic susceptibility between the matrix and the fluid. It generally depends on both pore geometry and the type of rock (mineralogy). The internal gradient can, in principle, be significant. It is independent of TE and dependent on field strength $$G_{int} \sim \frac{\Delta \chi \cdot B_0}{r_{pore}}$$

and is thus frequency dependent ($\Delta_\chi$ represents the difference in the magnetic susceptibility between the fluid and the solid matrix, and $r_{pore}$ represents the effective radius of the pores in the matrix). However, within the current operating range of the NMR logging tool, $B_0$ varies within a factor of 2 and the variation of the internal field gradient is also limited to this range. More importantly, the time and ensemble averaging of the random orientation of $G_{int}$ eliminates the term $<G_{int}G_{ext}>$. The phase displacement is thus proportional to the sum of the squares of the internal and external gradients (Eq. (5)).

$$(\vec{G}_{total})^2 = G_{int}^2 + G_{ext}^2 + 2\langle G_{int}G_{ext}\rangle \approx G_{int}^2 + G_{ext}^2, \quad (5)$$

Thus, the diffusion decay rate of Eq. (3), which is a function of gradient, can be separately described as being due to internal and external gradient, respectively:

$$T_{2Diff}^{-1} = T_{2Diff,int}^{-1} + T_{2Diff,ext}^{-1} = \frac{\gamma^2 G_{int}^2 TE^2 D_{fluid}}{12} + \frac{\gamma^2 G_{ext}^2 TE^2 D_{fluid}}{12}. \quad (6)$$

The effect of the internal gradient in Eq. (2) can be embedded into the rest of terms:

$$T_2^{-1} = \left[T_{2B}^{-1} + \rho\frac{S}{V} + T_{2Diff,int}^{-1}\right] + T_{2Diff,ext}^{-1} \quad (7)$$

The term in brackets in Eq. (7) is independent of the external gradient. The internal gradient strength variation is linearly proportional to the frequency variation as $$G_{int} \propto B_0 \propto f$$

while the external gradient variation is greater than the linear proportionality of f. For most case where on the average $$\overline{G}_{ext} >> \overline{G}_{int}$$

and $T_{2Diff,int}^{-1}$ does not dominate the term in the square bracket, we may make the approximation that the quantity in the square bracket of Eq. (7) is frequency independent. Thus, if all the data to be combined have the same TE, the term in brackets is regarded to be approximately the same for all multiecho sequences. If the TE values of these multiecho sequences are different, the term in the bracket is approximately valid only if the decay term due to internal gradient is much smaller than that of the bulk and surface relaxation terms combined or is much smaller than the external gradient term. These conditions are practically and approximately valid in many cases. In the following paragraphs, the gradient refers to only the external gradient.

Typically, a multiecho sequence acquired at frequency $f_j$ in a gradient field $G_j$, is represented using a multiexponential model:

$$E(f_j, k, TE) = \sum_i^{N\_comp} M_i \cdot \exp(-k \cdot TE / T_{2i}) \cdot \exp\left(-k \cdot TE \cdot \frac{\gamma^2 G_j^2 TE^2 D_{fluid}}{12}\right) \quad (8)$$

where i,j,k are indices for the $i^{th}$ $T_2$ component, $j^{th}$ frequency, and $k^{th}$ echo, respectively. N_comp refers to the number of $T_2$ components. A standard multiecho sequence shown in Eq. (9) is thus denoted $E_S$, and the multiecho sequence of the capillary bound water, which has a length shorter than the standard multiecho sequence, shown in Eq. (10) is denoted $E_B$ herein.

$$E_S(f_S, k, TE) = \sum_i^{N\_comp} M_i \cdot \exp(-kTE/T_{2i}) \cdot \exp\left(-kTE \cdot \frac{\gamma^2 G_s^2 TE^2 D_{fluid}}{12}\right) \quad (9)$$

$$E_B(f_B, k, TE) \approx \sum_i^{N\_comp} M_i \cdot \exp(-kTE/T_{2i}) \cdot \exp\left(-kTE \cdot \frac{\gamma^2 G_B^2 TE^2 D_{fluid}}{12}\right) \quad (10)$$

$E_S$ and $E_B$ are acquired using frequencies $f_S$ and $f_B$, respectively. The number of echoes, NE, of the two multiecho sequences may be different, with $NE_B \leq NE_S$. The same TE is used for both multiecho sequences, and both sequences are fully polarized. Typically, the multiecho sequences for the capillary bound water are not stacked with the standard multiecho sequence. However, correcting the echo amplitude discrepancy on $E_B$ due to gradient effect enables $E_S$ and $E_B$ to be stacked together. If, however, $NE_B << NE_S$ and $NE_B \cdot TE_B$ is small, the maximum gradient effect is insignificant if $$\exp\left(-NE_B \cdot TE_B \frac{\gamma^2 \cdot G^2 \cdot TE_B^2 D_i}{12}\right) \approx 1$$

so that the gradient correction can be avoided.

In a preferred method of the invention, the longest multiecho sequence is acquired using the highest frequency, since the highest frequency produces the best signal-to-noise ratio (SNR). Thus, $f_S > f_B$ typically. However, the choice of which frequency is used to acquire the longest multiecho sequence is not to be considered as a limitation of the invention.

A variety of petrophysical parameters can be found using the methods fo the present invention. For example, if two multiecho sequences, A and B, differ only in the wait time (TW), these two multiecho sequences can be averaged together. The resultant equation is $$\overline{E} = \left(\frac{w_A A + w_B B}{w_A + w_B}\right) = \sum_{i=1}^{N} M_i \exp\left(-\frac{kTE}{T_{2i}}\right) \exp\left(-kTE \frac{\gamma^2 G^2 TE^2 D_i}{12}\right) \left(\frac{w_A p_{A,i} + w_B p_{B,i}}{w_A + w_B}\right)$$

where $w_A$ and $w_B$ are the weights for the signals A and B, respectively. Polarization factors are for signals A and B are shown as $p_{A,i}$ and $p_{B,i}$. For a very long TW, the signals are fully polarized (p=1). Otherwise, 0<p<1. The equation can be used to obtain the fully polarized partial porosity, such as CBW, or capillary bound water. The rest of the partial polarized signal can be discarded.

If two multiecho sequences, A and B, differ only in their frequencies and the tool magnetic field gradient results in negligible difference among all k in the term:

$$\exp\left(-kTE \frac{\gamma^2 \cdot G^2 \cdot TE^2 D_i}{12}\right)$$

for those two frequencies, then these two multiecho sequences can be weight-averaged together and the resultant can be used to obtain the entire porosity distribution, using:

$$\overline{E} = \left(\frac{w_A A + w_B B}{w_A + w_B}\right) = \sum_{i=1}^{N} M_i \exp\left(-\frac{kTE}{T_{2i}}\right) \exp\left(-kTE \frac{\gamma^2 G^2 TE^2 D_i}{12}\right)$$

If two multiecho sequences, A and B, differ by G only, the two multiecho sequences can be weight-averaged together after a gradient correction is applied, and the resultant can be used to obtain the total porosity, effective porosity, CBW, capillary bound water volume, and BVM, utilizing $$\overline{E} = \left(\frac{w_A A + w_B B'}{w_A + w_B}\right) \approx \sum_{i=1}^{N} M_i \exp\left(-\frac{kTE}{T_{2i}}\right) \exp\left(-kTE \frac{\gamma^2 G_A^2 TE^2 D_i}{12}\right)$$

where B' is the gradient corrected multiecho sequence B. The gradient correction consists of computing the correction factor according to the two G values and the water diffusivity at given temperature and pressure. A time-dependent weighting factor, as described previously, is applied to the individual echoes of the two multiecho sequences.

If the two multiecho sequences, A and B, differ in G*TE, due to either (1) only TE being different, or (2) both G and TE being different, a correction of G*TE effect can be applied, followed by an interpolation to bring the data points to the same data density, TE, and application of a time-dependent weight function before averaging. The applied weights depend on TE, the standard deviation of noise, and the G*TE correction factor and is performed as described previously. Multiecho sequences that are weight averaged and G*TE corrected are used only for obtaining formation parameters, but not for obtaining fluid properties.

Figure 6:
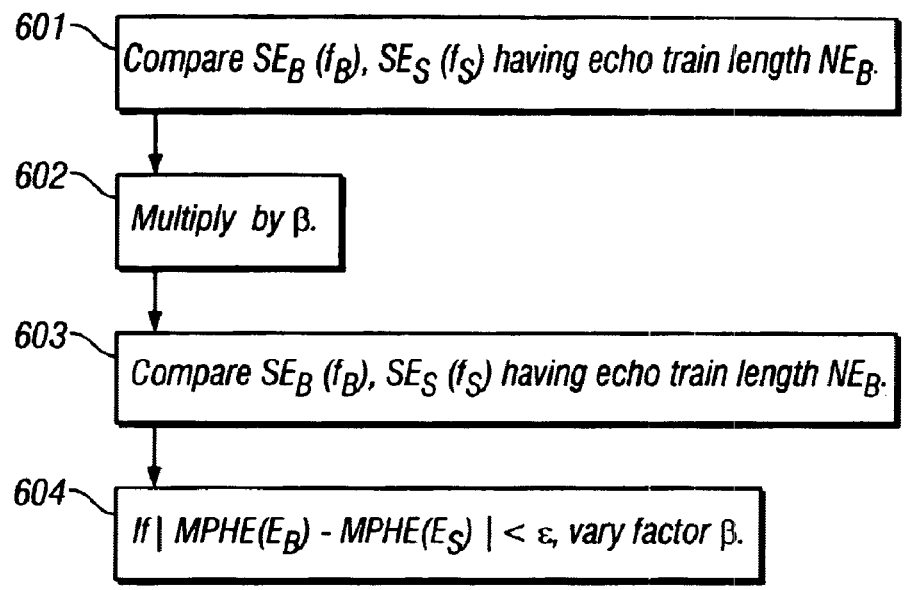
FIG. 6 shows a flowchart of the preferred method of the invention.

FIG. 6 shows a flowchart of a preferred method of the invention. In Box 601, a comparison is made between the summations of the standard multiecho sequence $SE_S(f_S)$ and the BVI multiecho sequence $SE_B(f_B)$. $SE_S(f_S)$ has a corresponding echo length $NE_S$ and $SE_B(f_B)$ has a corresponding echo length $NE_B$. Comparison is made by taking the minimum number of echoes $(\min\{NE_B, NE_S\})$ and summing up each multiecho sequence from 1 to $\min\{NE_B, NE_S\}$. This summation is applied on a substantially large number of vertically-averaged echo data in order to remove the effects of random noise. If $SE_B(f_B)-SE_S(f_S) \leq 0$ in a consistent manner, no correction for noise is required. Otherwise, the method of the invention can be applied.

In Box 602, one multiplies multiecho sequence $E_B$ echo-by-echo by a factor of $$\beta = \exp\left(-k \cdot TE \cdot \frac{\gamma^2(G_S^2 - G_B^2)TE^2 D_{water}}{12}\right), \quad (11)$$

where k is the index of the echo. The $D_{water}$ and gradient values can be derived from knowledge of the corresponding reservoir temperature and activation frequencies. The result of this multiplication approximates the predicted $E_B$ in terms of $f_S$:

$$E_B(f_S,k,TE) \approx E_B(f_B,k,TE) \cdot \beta(TE, D_{water},f_B, f_S) \quad (12)$$

In Box 603, one compares $SE_B(f_B)$ and $SE_S(f_S)$ Comparison is made by taking the minimum amount of echoes $(\min\{NE_B,NE_S\})$ and summing up each multiecho sequence from 1 to $\min\{NE_B,NE_S\}$. This summation is applied on a substantially large number of vertically-averaged data to remove the effects of random noise. If the difference is larger than a determined tolerance, one proceeds to Box 604.

In Box 604, one compares effective porosity (MPHE) obtained from $T_2$ values derived from $E_B(f_S,k,TE)$ and $E_S(f_S,k,TE)$. This comparison is applied on a substantially large number of vertically-averaged data in order to remove the effects of random noise. If $|MPHE(E_B)-MPHE(E_S)| \leq \epsilon$ (tolerance) and $SE_B(f_S) > SE_S(f_S)$, this indicates under-correction. For under correction, one increases $G_S^2-G_B^2$, as seen in the equation for β, by a factor slightly larger than 1, and reprocesses. If $|MPHE(E_B)-MPHE(E_S)| \leq \beta$(tolerance) and $SE_B(f_S) < SE_S(f_S)$, this indicates over-correction. For over-correction, one reduces the gradient $G_S^2-G_B^2$ by a factor slightly smaller than unity, and reprocesses.

The procedure outlined in the flowchart of FIG. 6 is applicable to those multiecho sequences that are acquired with a same TE but at a different frequency (and gradient). In another embodiment where TE differs between multiecho sequences and frequency may be same or different from each other, an alternate method is applicable by using a small modification of the summation of echoes by replacing SE with SE/TE.

Figure 7A:
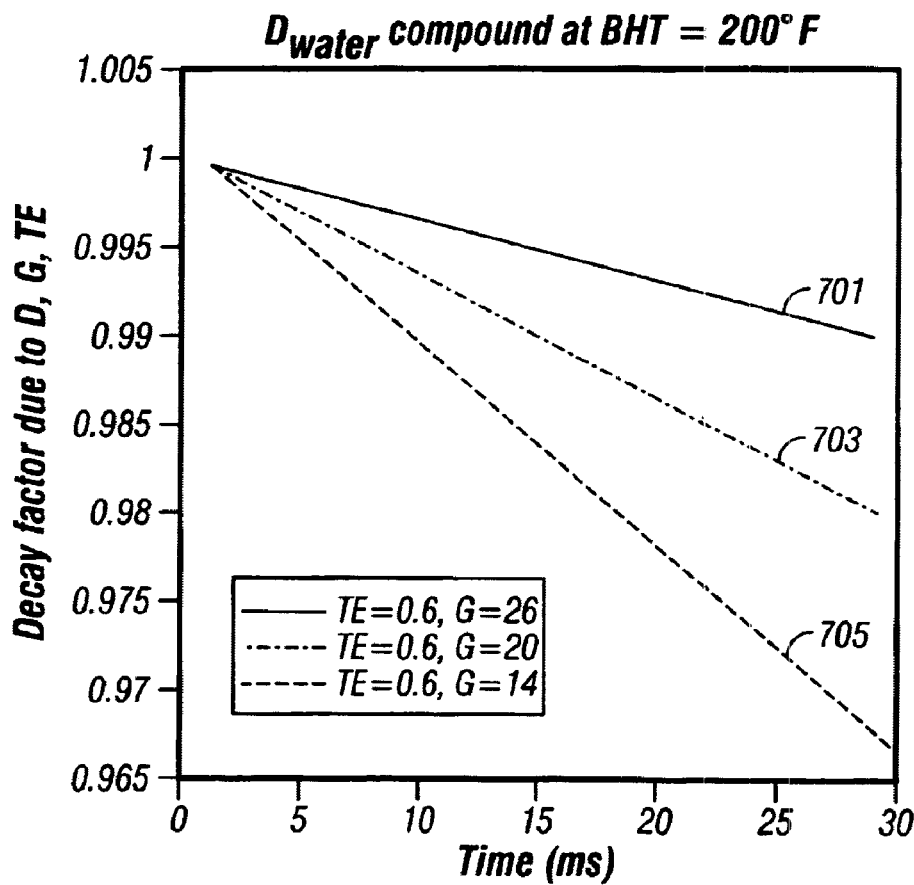
FIGS. 7a-d show examples of the echo decay due to diffusion in a gradient field.
Figure 7B:
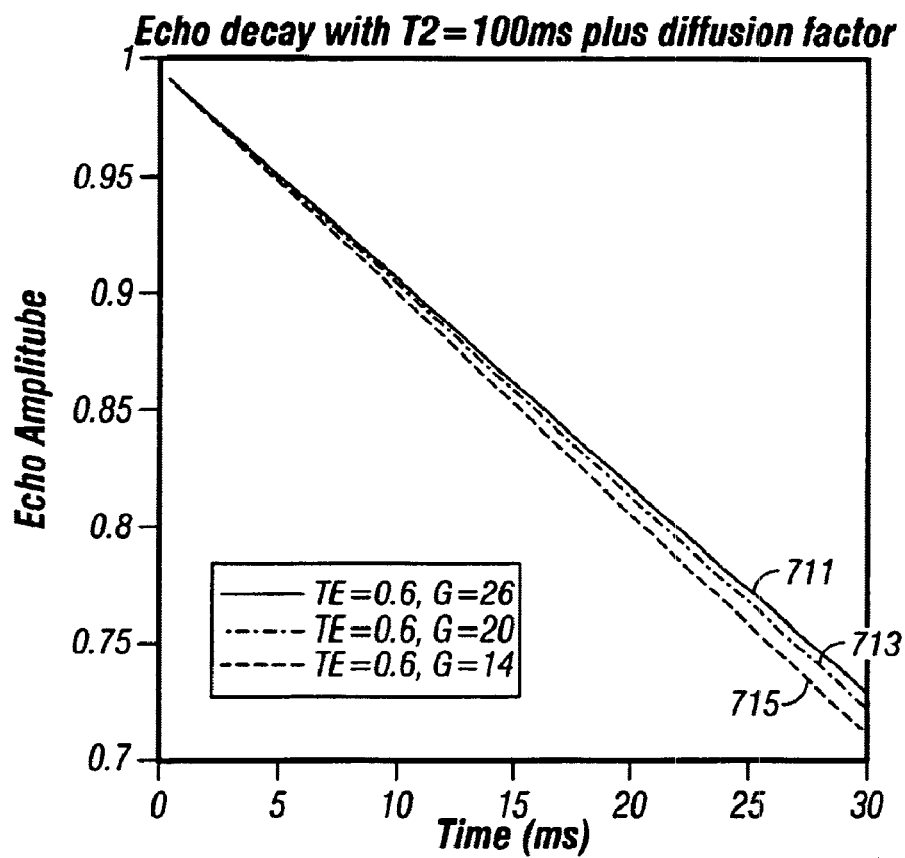
Figure 7C:
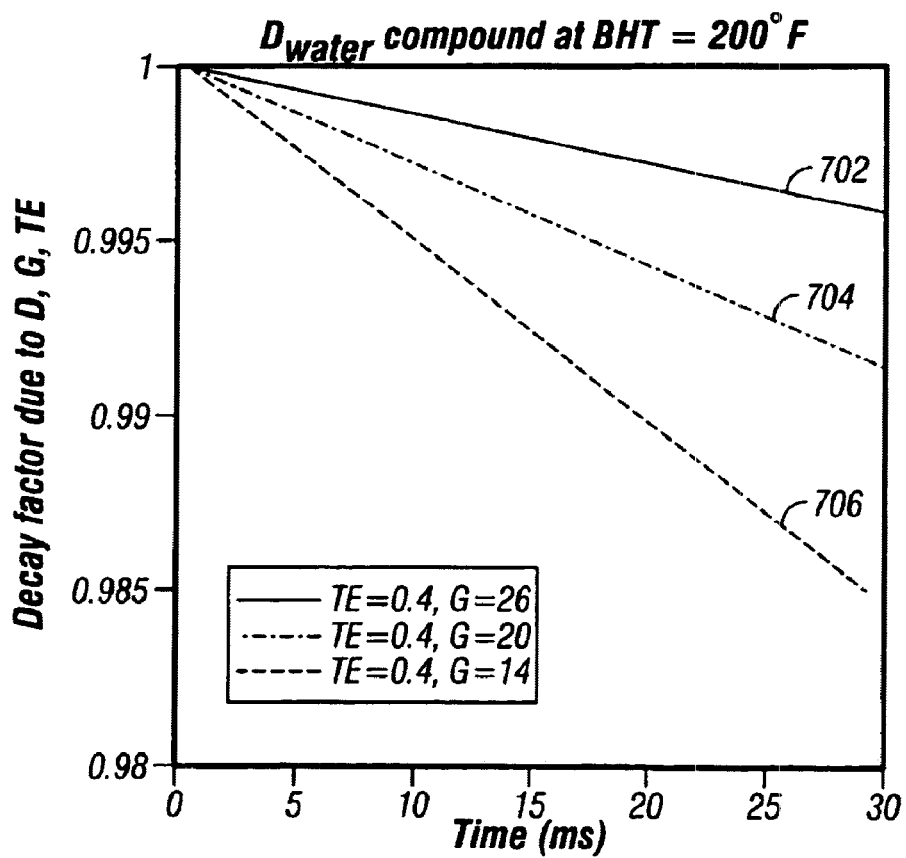
Figure 7D:
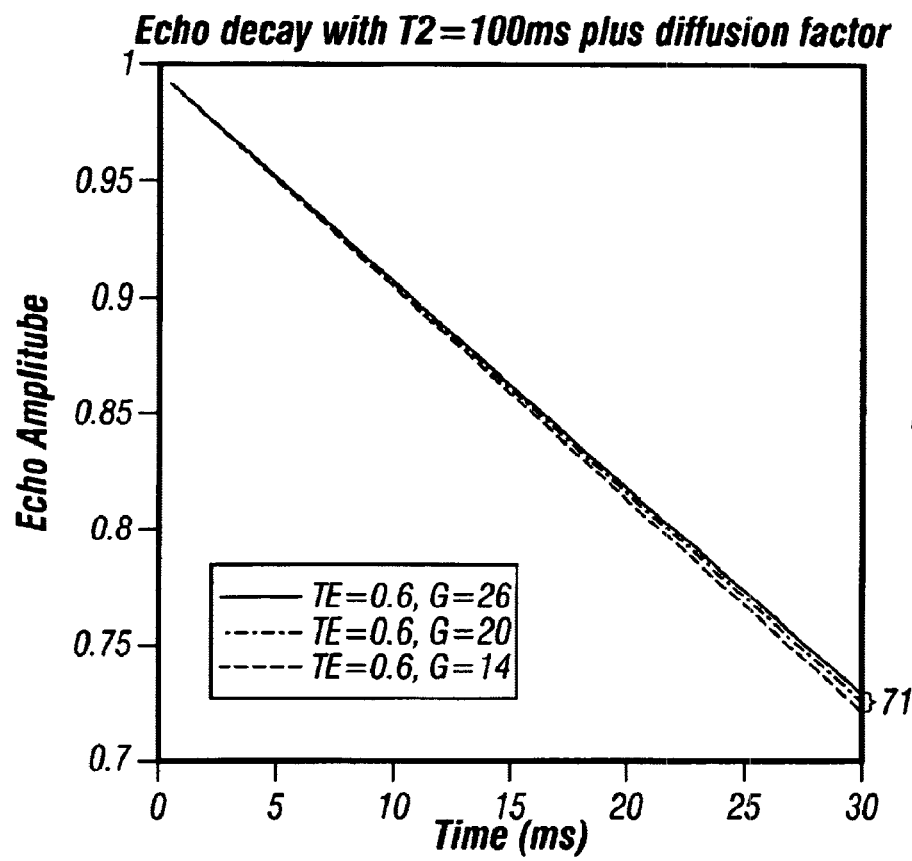

FIGS. 7a-d exemplifies the echo decay due to diffusion in a gradient field. The simulated data is consistent with a test tool magnet and gradient configuration operating substantially in the frequency range of 425 kHz to 800 kHz. Frequencies are defined roughly at 12 discrete frequency numbers, with the lowest frequency being indicated by #1 and the highest by #12. Use of the simulated data is meant only as an example, is not necessarily limited to the above-mentioned frequency range, and is not meant as a limitation of the invention. Typically, at TE=0.6 ms or less for all frequencies, the gradient effect for the first 30 ms of echo data is insignificant. FIGS. 7a-d illustrates the effect of gradient on a 100 ms $T_2$ component. A $T_2$ value of 100 ms can be used for illustrative purposes because it is the geometric mean of two equally weighted components of 10 ms and 1000 ms, respectively. The effects of parameters D, G, and TE on the decay factor can be seen in FIGS. 7a and 7c. In FIG. 7a, TE=0.6 ms and G-values are set at 14, 20, and 26 Gauss/cm (curves 701, 703, and 705 respectively). The decay factor is measured along the ordinate, and time (in msec) is measured along the abscissa. In FIG. 7c, TE=0.4 ms and G-values are set at 14, 20, and 26 Gauss/cm, (curves 702, 704, and 706, respectively). The decay factor is measured along the ordinate, and time (in msec) is measured along the abscissa. The effects shown in FIG. 7a can be seen on the decay of the echo amplitude in FIG. 7c, and the effects shown in FIG. 7c can be seen on the decay of the echo amplitude in FIG. 7d. FIG. 7b shows a discrepancy of less than 2.5% in the 30 ms in the echo decay data for applied gradients between 14 Gauss/cm (711), 20 Gauss/cm (713), and 14 Gauss/cm (715) at TE=0.6 ms. Echo amplitude is measured along the ordinate and time (in msec) is measured along the abscissa. As seen in FIG. 7d (having the same axes as FIG. 7b), this discrepancy reduces to 2% at TE=0.4 ms, where curves represent G=26, 30, and 14 Gauss/cm are substantially the same (716). The gradient difference shown is larger than that between frequency indices #3 and #10. In other cases (i.e. the FE3 case discussed in U.S. patent application Ser. No. 10/288,115, filed Nov. 5, 2002 by *Chen and Edwards*, the contents of which are fully incorporated herein by reference and and having the same assignee as the present application), the effect can be even less than that illustrated in FIGS. 7b and 7d.

If frequency #9 is used for the longest multiecho sequence, and frequencies #6 and #12 are used for the fully polarized multiecho sequences of the capillary bound water, the stacked results have an average decay effect that is approximately $$decay_{avg} = \frac{1}{3}\begin{bmatrix} \exp(-(nTE)TE^2\gamma^2 G_6^2 D/12) + \\ \exp(-(nTE)TE^2\gamma^2 G_9^2 D/12) + \\ \exp(-(nTE)TE^2\gamma^2 G_{12}^2 D/12) \end{bmatrix}$$

$$\approx 1 - (nTE)TE^2\gamma^2(G_6^2 + G_9^2 + G_{12}^2)D/36$$

$$= 1 - (nTE)TE^2\gamma^2(G_9^2)D/12 +$$

$$(nTE)TE^2\gamma^2(2G_9^2 - G_6^2 - G_{12}^2)D/36$$

$$= decay_9 + \Delta$$

Therefore, the echo decay difference between the three-frequency averaged data and the middle frequency (#9) is given by $$\Delta = (nTE)TE^2\gamma^2 (2G_9^2-G_6^2-G_{12}^2)D/36.$$

If the following approximation is used:

$$G_{12}-G_9 \approx G_9-G_6 \equiv dG, \text{ then}$$

$$\Delta \approx -\frac{2}{3} \cdot (nTE)TE^2\gamma^2 dG^2 D/12$$

Since $G_9$ is ~26 Gauss/cm and if dG is ~6 Gauss/cm, the effect produces an insignificant factor for CBW type multiecho sequence with NE·TE=10 ms and a small factor for clastic $T_{2cutoff}$ of 33 ms, but a significant difference for standard multiecho sequence with NE·TE=500 ms.

Figure 8:
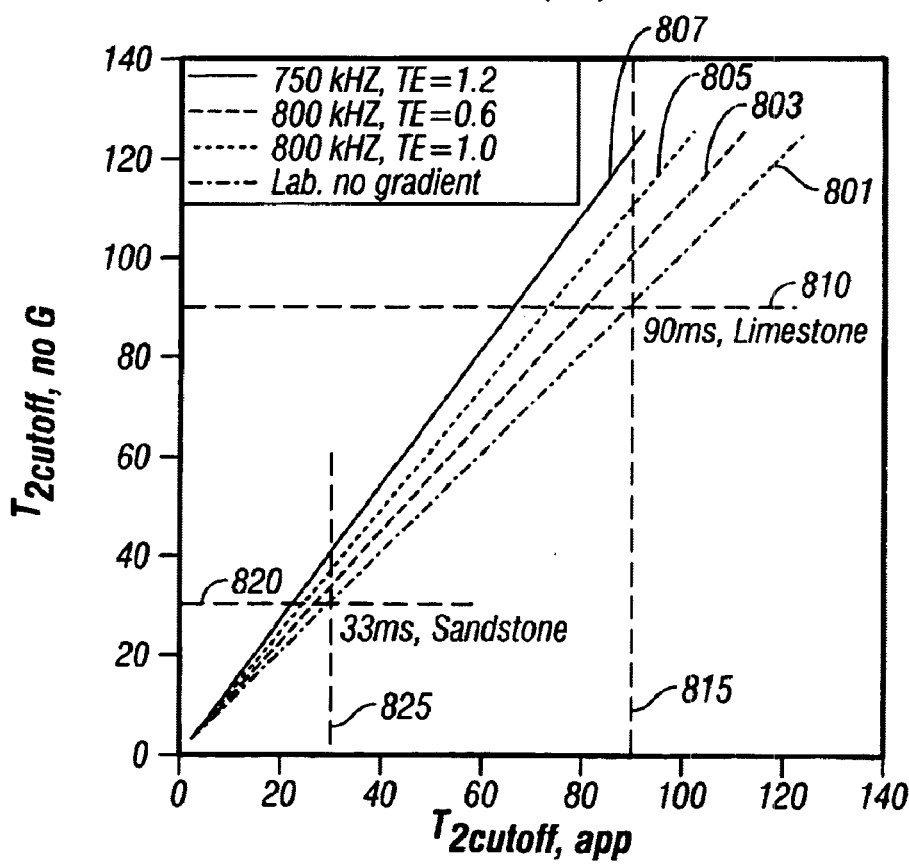
FIG. 8 shows the discrepancy between $T_{2cutoff}$ values derived in a laboratory setting with no applied gradient, and in the gradient tool environment.

FIG. 8 shows the discrepancy between $T_{2cutoff}$ values derived in a laboratory setting with no applied gradient 801, and the apparent $T_{2cutoff}$ found in a gradient tool environment with the gradient values shown in FIG. 5b. All data in FIG. 8 assume a 200° F. temperature environment. The intercepts of horizontal lines 810 and 820 with the $T_{2cutoff}$ curves, 801, 803, 805, and 807, represent the equivalent $T_{2cutoff}$ values that should be used in log data interpretation if the standard sandstone or limestone $T_{2cutoff}$ values, derived from lab data, are used. The intercepts of the vertical lines with the $T_{2cutoff}$ curves represent the equivalent lab $T_{2cutoff}$ values if 33 ms (825) or 90 ms (815) cutoff values are used to interpret log data.

The example in FIG. 8 is based on a tool gradient of up to 26 Gauss/cm. If a tool operates at a higher gradient field, the equivalent $T_{2cutoff}$ may be lower than 33 ms for a large G·TE combination. In this case, the correction is necessary.

In another embodiment of the invention, two multiecho sequences are acquired at two different frequencies (and thus at two different gradients G) and two different TE. The two sequences can be combined by first modifying Eq. (11) to include the TE differences $$\zeta(t) = \exp\left(-k \cdot TE_S \cdot \frac{\gamma^2(G_S^2 TE_S^2 - G_B^2 TE_B^2)D_{water}}{12}\right) \quad (13)$$

for the $k^{th}$ echo in a CPMG multiecho sequence at time $t = k \cdot TE_S$. The two multiecho sequences again can have either the same or different lengths, NE·TE. To apply the correction, the multiplier from either Eq. (11) or Eq. (13), depending on the applicability, is applied to the measured echo signal, M(t), which includes both the signal, S(t), and noise, N(t), for the individual echo contaminated with random noise:

$$\Re(t) = M(t)\zeta(t) = S(t)\zeta(t) + N(t)\zeta(t)$$

The second term (noise term) indicates that the noise may be also amplified (or reduced) by the same factor as the signal. In order to perform averaging on this data with others, a time dependent weight factor of $\beta^{-2}(t)$ or $\zeta^{-2}(t)$ is applied to the multiecho sequence M(t) such that $$\langle \Re(t) \rangle = \frac{\sum_l \Re_l(t)/\zeta_l(t)^2}{\sum_l \zeta_l(t)^{-2}} \quad (14)$$

and a similar treatment can be used if the correction factor is $\beta$. Thus, for those echoes having a very large t, occurring at the end of a long multiecho sequence, the weighting factor is very small. This corresponds to a signal whose strength is comparable to that of the noise level.

The invention further enables an analysis when standard deviation of noise differs from that of the original multiecho sequences. The weights should be further modified by multiplying $\beta$ or $\zeta$, with the standard deviation of noise for the $l^{th}$ multiecho sequence, $\sigma_l$. Also, a difference in data sampling rate, due to TE being different between original multiecho sequences, can be included as an additional factor through the equation $$\xi_l(t) = \zeta_l(t) \cdot \sigma_l \cdot \sqrt{TE_l}$$

Thus, when all these factors are considered the weighting factor is $$\langle \Re(t) \rangle = \frac{\sum_l \Re_l(t)/[\zeta_l(t)^2 \sigma_l^2 TE_l]}{\sum_l \zeta_l(t)^{-2} \sigma_l^{-2} TE_l^{-1}} = \frac{\sum_l M_l(t)/[\zeta_l(t)\sigma_l^2 TE_l]}{\sum_l \zeta_l(t)^{-2} \sigma_l^{-2} TE_l^{-1}} \quad (14)$$

Figure 9:
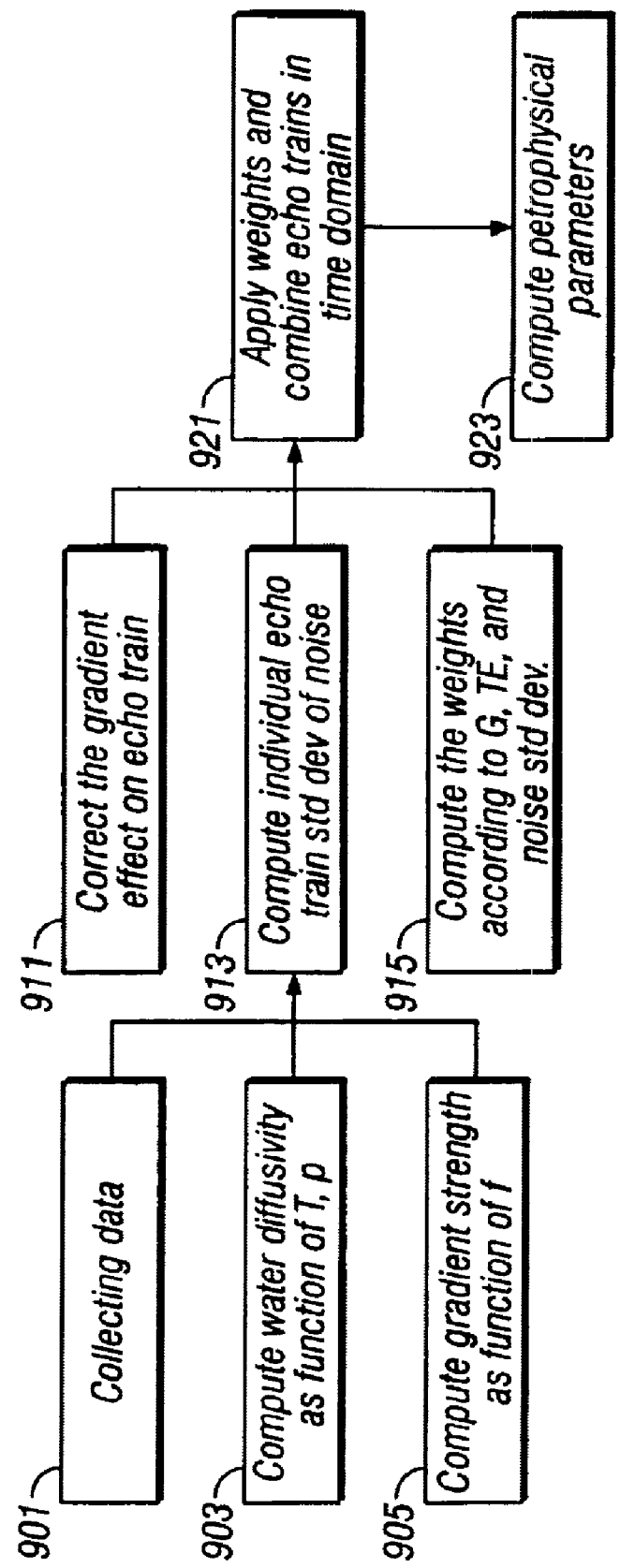
FIG. 9 shows a flowchart of a method of the present invention under variation of multiple parameters.
Figure 5A:
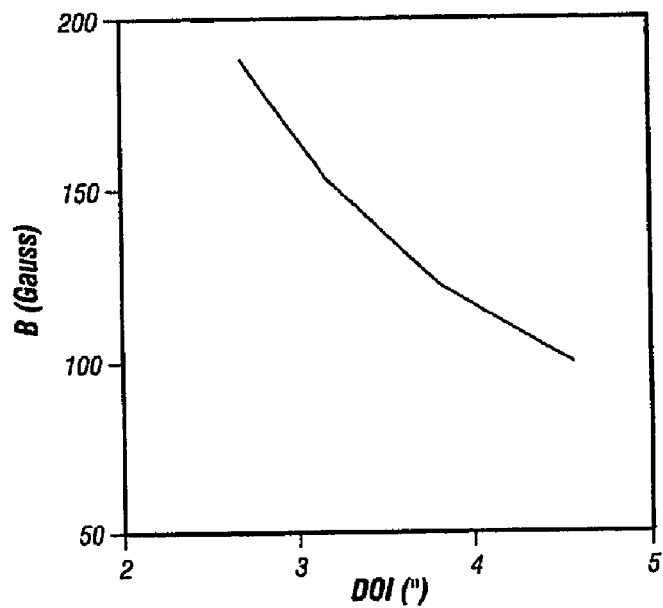
Figure 5B:
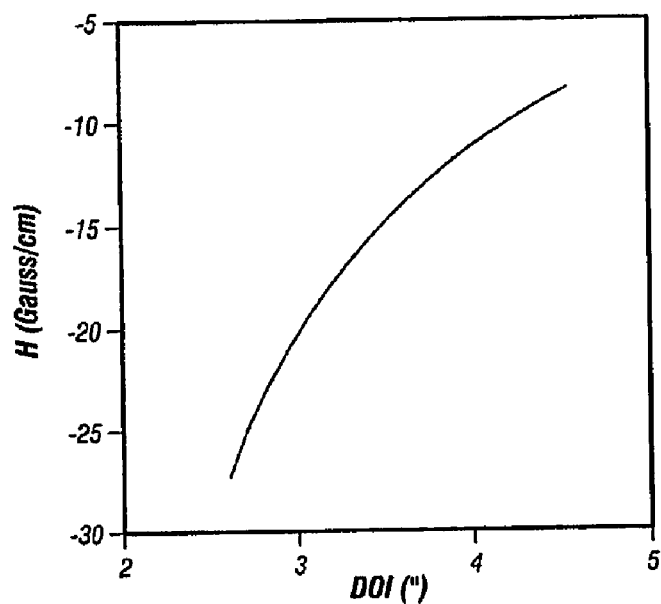
Figure 9:
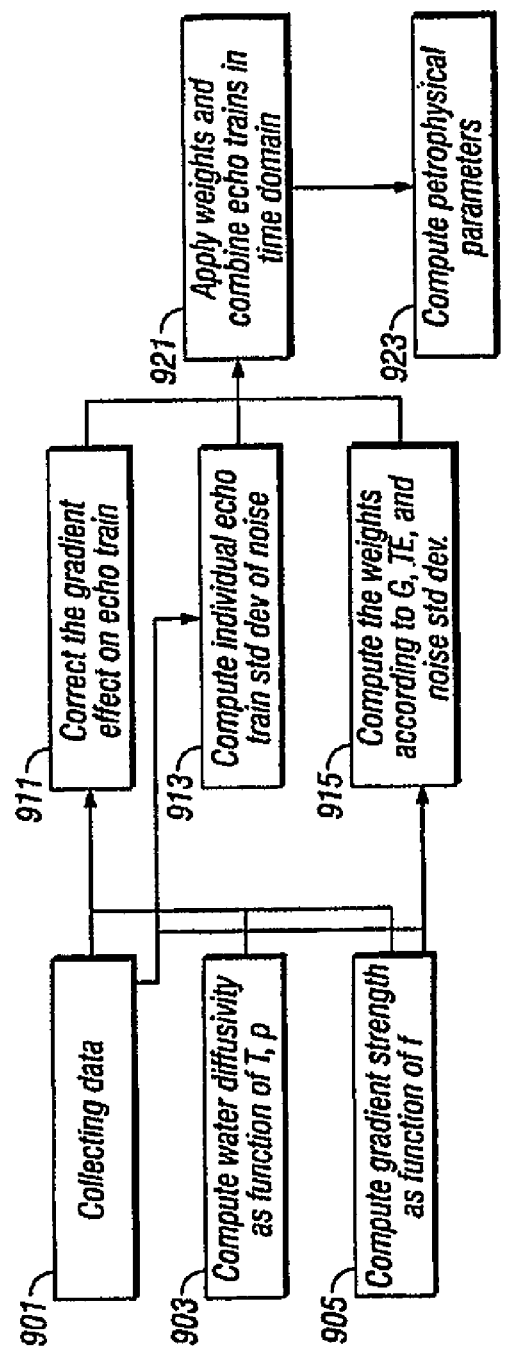

FIG. 9 shows a flowchart of a method of the present invention for the method under variation of multiple parameters, such as gradient, inter-echo spacing, and standard deviation. NMR data is collected in Box 901 and a computation is made for the diffusivity of water Box 903. Diffusivity is determined as a function of temperature and pressure at a given depth. The gradient strength is computed as a function of frequency in Box 905. With the data of Boxes 901, 903, and 905, a correction is made for the effect of the gradient on the multiecho sequence in Box 911. Individual standard deviations of noise in multiecho sequences can be computed in Box 913. In Box 915, one computes the weights, such as those described in Eq. (12), according to the parameters involved (G, TE, and the standard deviation of the noise). In Box 921, one applies the weights of Box 915 and combines the multiecho sequences in the time domain. The results of Box 921 enable the operator towards a computation of petrophysical parameters in Box 923.

The present invention has been described with reference to a wireline, multi frequency logging device. However, the method of the present invention may also be used on a logging while drilling (LWD) device forming part of a bottom hole assembly conveyed on a drilling tubular. It may specifically be used with a single frequency device.

While the foregoing disclosure is directed towards the preferred embodiment of the invention, various modifications will be apparent to those skilled in the art. It is intended that all variations within the scope and spirit of the appended claims be embraced by the foregoing disclosure.

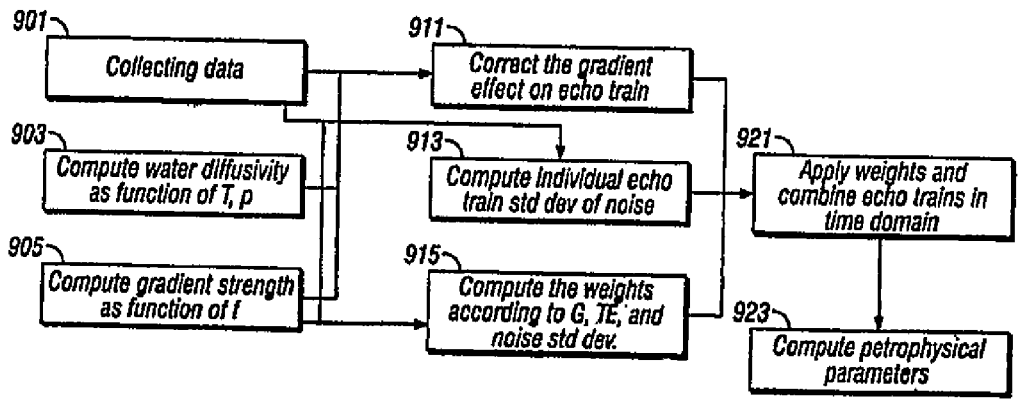

What is claimed is:

1. A method of logging of an earth formation using an logging tool conveyed in a borehole in said formation, the method comprising:
    (a) acquiring a first multiecho sequence from a first region of interest using a first radio frequency (RF) pulse sequence;
    (b) acquiring a second multiecho sequence from a second region of interest using a second RF pulse sequence;
    (c) determining at least one correction factor depending at least in part on a diffusivity of a fluid in said earth formation; and
    (d) combining said first and second multiecho sequences using said at least one correction factor to obtain a combined multiecho sequence, wherein at least one of the following conditions exists:
        (A) said second RF pulse sequence has at least one parameter different from a parameter of aid first RF pulse sequence; and
        (B) a gradient of a static magnetic field in said first region is different from a gradient of a static magnetic field in said second region.

2. The method of claim 1 wherein said second region is the same as the first region.

3. The method of claim 1 wherein said second region is different from the first region.

4. The method of claim 1 wherein said logging tool is a multifrequency logging tool, and a static magnetic field in said first region is different from a static magnetic field in said second region.

5. The method of claim 1 further comprising using a field shifting arrangement on said logging tool for shifting a static magnetic field in the earth formation.

6. The method of claim 1, wherein said at least one parameter is at least one of: (i) frequency, (ii) an interval between refocusing pulses, (iii) a polarization time, and, (iv) a number of pulses.

7. The method of claim 1, wherein said at least one correction factor is a multiplicative factor relating the first and second multiecho sequences.

8. The method of claim 1, wherein said at least one correction factor is further dependent on at least one of: (i) a gradient of a static magnetic field associated with said first RF pulse sequence, (ii) a gradient of a static magnetic field associated with said second RF pulse sequence, (iii) an interecho time associated with said first RF pulse sequence, (iv) an interecho time associated with said second RF pulse sequence, (v) a noise level for said first multiecho sequence, and, (vi) a noise level for said second multiecho sequence.

9. The method of claim 1, further comprising obtaining said fluid diffusivity from a measured diffusivity and applying a correction for at least one of: (i) a temperature of the fluid, and, (ii) a depth of the fluid.

10. The method of claim 1, wherein said first and second RF pulse sequences have substantially the same frequency and substantially the same interecho time, and said at least one correction factor is given by a relation of the form $$\beta = \exp\left(-k \cdot TE \cdot \frac{\gamma^2 (G_S^2 - G_B^2) TE^2 D}{12}\right)$$

where k is an echo index, TE is an inter-echo spacing, γ is the gyromagnetic ratio, $G_S$ is a gradient of a static magnetic field corresponding to the first multiecho sequence, $G_B$ is a gradient of a static magnetic field corresponding to the second multiecho sequence, and D is a fluid diffusivity.

11. The method of claim 1, wherein said at least one parameter comprises different frequencies and different values of TE and said at least one correction factor is given by a relation of the form $$\zeta(t) = \exp\left(-k \cdot TE_S \cdot \frac{\gamma^2 (G_S^2 TE_S^2 - G_B^2 TE_B^2) D_{water}}{12}\right)$$

where k is an echo index of the echo, $TE_S$ is an inter-echo spacing corresponding to the first pulse sequence, $TE_B$ is an inter-echo spacing corresponding to the second pulse sequence, γ is the gyromagnetic ratio, $G_S$ is a gradient of a static magnetic field corresponding to the first pulse sequence, $G_B$ is a gradient of a static magnetic field corresponding to the second pulse sequence, and $D_{water}$ is the water diffusivity.

12. The method of claim 1, wherein there is a difference in a noise level of the first multiecho sequence and the second multiecho sequence, and wherein said at least one correction factor is dependent on one of said noise levels.

13. The method of claim 1, wherein there is a difference an interecho spacing of said first multiecho sequence and an interecho spacing of said second multiecho sequence, and wherein said at least one correction factor is dependent on one of said interecho spacings.

14. The method of claim 1, wherein said at least one parameter comprises only a wait time, the method further comprising determining from said combined multiecho sequences a clay bound water and a capillary bound water volume.

15. The method of claim 1, wherein said at least one parameter comprises only a frequency, the method further comprising determining from said combined multiecho sequence an entire porosity distribution.

16. The method of claim 1, wherein first and second regions of interest differ in a gradient of an associated static magnetic field, the method further comprising determining from said combined multiecho sequence at least one of (i) an effective porosity, (ii) a clay bound water, and, (iii) a capillary bound water volume.

17. The method of claim 10 further comprising:
  (i) comparing a total porosity obtained from said first multiecho sequence and said second multiecho sequence,
  (ii) comparing a sum of echoes of the first and second multiecho sequence, and
  (iii) adjusting said correction factor based on said comparisons.

18. The method of claim 1, wherein a product of a gradient and an interecho time for the first region of interest is different from a product of a gradient and an interecho time for the second region of interest, the method further comprising:
  (i) applying an interpolation to bring data points to the same density, and
  (ii) applying a time-dependent weighting function.

19. An apparatus for use in an earth formation, the apparatus comprising:
  (a) a magnet on a logging tool conveyed in a borehole in said formation which produces a static magnetic field in a first and a second region of interest in said earth formation;
  (b) an antenna on the logging tool which produces a first and second radio frequency pulse sequence in said first and second regions;
  (c) an antenna on the logging tool which acquires a first and a second multiecho sequence from said first and second regions;
  (d) a processor which:
    (i) determines at least one correction factor depending at least in part on a diffusivity of a fluid in said earth formation; and
    (ii) combines said first and second multiecho sequences using said at least one correction factor to obtain a combined multiecho sequence, wherein at least on of the following conditions exists:
      (A) said second pulse sequence has at least one parameter different from a parameter of said first pulse sequence, and
      (B) a gradient of a static magnetic field in said first region is different from a gradient of a static magnetic field in said second region.

20. The apparatus of claim 19, wherein said fist and second regions are the same.

21. The apparatus of claim 19, wherein said first and second regions are different.

22. The apparatus of claim 19, wherein said logging tool is a multifrequency logging tool, and a static magnetic field in said first region is different from a static magnetic field in said second region.

23. The apparatus of claim 19, wherein said logging tool includes an arrangement for shifting a static magnetic field in the earth formation.

24. The apparatus of claim 19, wherein said at least one parameter is at least one of: (I) an interval between refocusing pulses, (II) a polarization time, and, (III) a number of pulses.

25. The apparatus of claim 19, wherein said correction factor is a multiplicative factor relating the first and second multiecho sequences.

26. The apparatus of claim 19, wherein said a least one correction factor is further dependent on at least one of: (I) a gradient of a static magnetic field associated with said first RF pulse sequence, (II) a gradient of a static magnetic field associated with said second RF pulse sequence, (III) an interecho time associated with said first RF pulse sequence, (IV) an interecho time associated with said second RF pulse sequence, (V) a noise level for said first multiecho sequence, and, (VI) a noise level for said second multiecho sequence.

27. The apparatus of claim 19, further comprising using said processor for obtaining said fluid diffusivity from a measured diffusivity and applying a correction for at least one of: (i) a temperature of the fluid, and, (ii) a depth of the fluid.

28. The apparatus of claim 19, wherein said first and second RF pulse sequences have substantially the same frequency and substantially the same interecho time, and said at least one correction factor is given by a relation of the form $$\beta = \exp\left(-k \cdot TE \cdot \frac{\gamma^2(G_S^2 - G_B^2)TE^2 D}{12}\right)$$

where k is an echo index, TE is an inter-echo spacing, $\gamma$ is the gyromagnetic ratio, $G_S$ is a gradient of a static magnetic field corresponding to the first RE echo sequence, $G_B$ is a gradient of a static magnetic field corresponding to the second RF echo sequence, and D is a fluid diffusivity.

29. The apparatus of claim 19, wherein said at least one parameter comprises different frequencies and different values of TE and said at least one correction factor is given by a relation of the form $$\zeta(t) = \exp\left(-k \cdot TE_S \cdot \frac{\gamma^2(G_S^2 TE_S^2 - G_B^2 TE_B^2)D_{water}}{12}\right)$$

where k is an echo index of the echo, $TE_S$ is an inter-echo spacing corresponding to the first RF pulse sequence, $TE_B$ is an inter-echo spacing corresponding to the second RF pulse sequence, $\gamma$ is the gyromagnetic ratio, $G_S$ is a gradient of a static magnetic field corresponding to the first pulse sequence, $G_B$ is a gradient of a static magnetic field corresponding to the second pulse sequence, and D is a fluid diffusivity.

30. The apparatus of claim 19, wherein there is a difference in a noise level of the first multiecho sequence and the second multiecho sequence, and wherein said at least one correction factor is dependent on one of said noise levels.

31. The apparatus of claim 19, wherein there is a difference an interecho spacing of said first multiecho sequence and an interecho spacing of said second multiecho sequence, and wherein said at least one correction factor is dependent on one of said interecho spacings.

32. The apparatus of claim 19, wherein said at least one parameter consists only of a wait time, the processor further determining from said combined echo sequence a clay bound water a capillary bound water volume.

33. The apparatus of claim 19, wherein said at least one parameter consists only of frequency, the processor further determining from said combined echo sequence an entire porosity distribution.

34. The apparatus of claim 19, wherein first and second regions of interest differ in a gradient of an associated static magnetic field, the processor further determining from said combined sequence at least one of: (i) an effective porosity, (ii) a clay bound water, and, (iii) a capillary bound water volume.

35. The apparatus of claim 27, wherein the processor further:
  (I) compares a total porosity obtained from said first multiecho sequence and said second multiecho sequence,
  (II) compares a sum of echos of the first and second multiecho sequence, and
  (III) adjusts said correction factor based on said comparisons.

36. The apparatus of claim 19, wherein a product of a gradient and an interecho time for the first region of interest is different from a product of a gradient and an interecho time for the second region of interest, and wherein the processor further:
  (I) applies an interpolation to bring data points to the same density, and
  (II) applies a time-dependent weighting function.

* * * * *

UNITED STATES PATENT AND TRADEMARK OFFICE
CERTIFICATE OF CORRECTION

PATENT NO. : 6,859,034 B2
APPLICATION NO. : 10/435419
DATED : February 22, 2005
INVENTOR(S) : Songhua Chen It is certified that error appears in the above-identified patent and that said Letters Patent is hereby corrected as shown below:

Title page
Please delete Fig. 9 and insert therefor the new Fig. 9 attached

Please delete Fig. 5A / Fig. 5B and insert therefor the new Fig. 5A / 5B attached Signed and Sealed this Eighteenth Day of September, 2007

JON W. DUDAS
*Director of the United States Patent and Trademark Office*

United States Patent
Chen

(10) Patent No.: US 6,859,034 B2
(45) Date of Patent: Feb. 22, 2005

(54) TIME-DOMAIN DATA INTEGRATION OF MULTIPLE GRADIENT, MULTIPLE TE ECHO TRAINS

(75) Inventor: Songhua Chen, Katy, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 10/435,419

(22) Filed: May 9, 2003

(65) Prior Publication Data
US 2004/0222791 A1 Nov. 11, 2004

(51) Int. Cl.⁷ .................................................. G01V 3/00
(52) U.S. Cl. .................................................. 324/303
(58) Field of Search .................................. 324/303, 306, 324/300, 318, 322

(56) References Cited

U.S. PATENT DOCUMENTS

| | | | |
|---|---|---|---|
| 4,710,713 A | 12/1987 | Strikman | 324/303 |
| 4,717,877 A | 1/1988 | Taicher et al. | 324/303 |
| 5,212,447 A | 5/1993 | Paltiel | 324/300 |
| 5,698,979 A | 12/1997 | Taicher et al. | 324/303 |
| 6,107,796 A | 8/2000 | Prammer | 324/303 |
| 6,316,940 B1 | 11/2001 | Akkurt | 324/303 |
| 6,366,087 B1 * | 4/2002 | Coates et al. | 324/303 |
| 6,377,042 B1 | 4/2002 | Menger et al. | 324/303 |
| 6,512,371 B2 * | 1/2003 | Prammer | 324/303 |
| 6,650,114 B2 * | 11/2003 | Kruspe et al. | 324/303 |
| 2002/0163334 A1 | 11/2002 | Hagiwara | 324/303 |
| 2003/0071617 A1 | 4/2003 | Kruspe et al. | 324/303 |

* cited by examiner

Primary Examiner—Louis Arana
(74) Attorney, Agent, or Firm—Madan, Mossman & Sriram, P.C.

(57) ABSTRACT

When NMR spin echo measurements are obtained with one or more of (i) different echo intervals, (ii) different static field gradients, (iii) different polarization times, or (iv) noise levels, due to fluid diffusivity, the spin echo measurements cannot be simply combined. However, by applying a correction factor, such a combination is possible, giving an improved interpretation of the formation properties.

36 Claims, 8 Drawing Sheets